United States Patent [19]

Birum et al.

[11] 4,081,463
[45] Mar. 28, 1978

[54] PRODUCTION OF 2-CARBOXYETHYL(PHENYL)PHOSPHINIC ACID

[75] Inventors: Gail H. Birum, Kirkwood; Richard F. Jansen, Oakville, both of Mo.

[73] Assignee: Monsanto Company, St. Louis, Mo.

[21] Appl. No.: 755,363

[22] Filed: Dec. 27, 1976

[51] Int. Cl.$^2$ .............................................. C07F 9/30
[52] U.S. Cl. ........................ 260/502.4 R; 260/544 R; 260/545 P
[58] Field of Search ................................ 260/502.4 R

[56] References Cited
PUBLICATIONS

Pudovik et al., "Zhur. Obsch. Kim.," 37, No. 2, (1967), pp. 425–427.
Pudovik et al., "Russian Chemical Reviews," vol. 37, No. 5, (1968), pp. 317–332.
Wagner et al., "Synthetic Organic Chemistry," (1953), pp. 558–559.

Primary Examiner—Joseph E. Evans
Attorney, Agent, or Firm—Herman O. Bauermeister

[57] ABSTRACT

2-Carboxyethyl(phenyl)phosphinic acid is prepared in two stages by first reacting dichloro(phenyl)phosphine with acrylic acid employed at a molar excess of 25% to 45% to form a mixture of three intermediates, namely 3-(chlorophenylphosphinyl)propionyl chloride, the cyclic anhydride of 2-carboxyethyl(phenyl)phosphinic acid and the mixed anhydride of acrylic acid with 3-chlorocarbonylethyl(phenyl)phosphinic acid. The second stage of the process is the hydrolysis of the mixture of three intermediates set forth above to obtain the desired product. The product is useful as a flame retardant material when used with organic polymers such as polyesters.

4 Claims, No Drawings

PRODUCTION OF 2-CARBOXYETHYL(PHENYL)PHOSPHINIC ACID

BACKGROUND OF THE INVENTION

2-Carboxyethyl)phenyl)phosphinic acid, a flame retardant additive for polymers such as polyesters, has been prepared by first reacting of acrylic acid with dichloro(phenyl)phosphine. However, the reactants have been used in molar equivalent proportions, after which the addition product, 3-(chlorophenylphosphinyl) propionyl chloride, was isolated by a difficult distillation. This addition product was then subjected to a separate hydrolysis step to obtain the 2-carboxyethyl(phenyl)phosphinic acid in yield insufficient for commercialization, A. N. Padovik et al, "Reaction of Phenylphosphous dichloride with Acrylic Acid," Zhural Obshohei Khimii, 37, No. 2, pages 423–427 (1967).

SUMMARY OF THE INVENTION

It has now been found that a greatly increased yield of 2-carboxyethyl(phenyl)phosphinic acid is obtained when a very specific ratio of reactants, that is 25 to 45% molar excess of acrylic acid with respect to dichloro(phenyl)phosphine, is used. This has been found to result in the formation of three intermediates, III-V, according to the general reaction shown below.

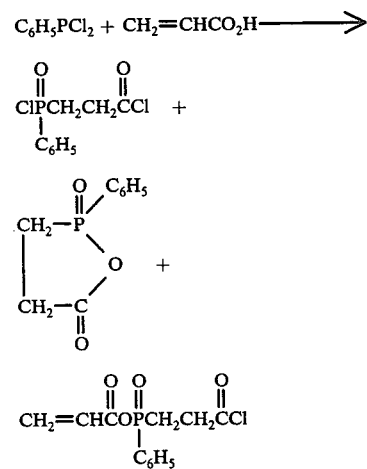

The proportions of the three intermediates vary with reaction conditions. The specific range of reactant proportions is critical, and it has been found that a quite different reaction product mixture results when only equivalent proportions of reactants are used. The conditions for the reaction are the use of a temperature of about 80° to 150° C, a preferred range being from 90° to 120° C. No catalyst is necessary for the reaction, nor is a solvent needed. However high boiling solvents such as toluene or monochlorobenzene may be used if desired.

The second stage of reaction is the hydrolysis of the above mixture of intermediates, preferably with 5 to 15 molar excess of water at 0° C to 100° C.

DETAILED DESCRIPTION OF THE INVENTION

It has now been found that the admixture of dichloro(phenyl)phosphine with excess acrylic acid produces not only the expected 3-(chlorophenylphosphinyl)propionyl chloride intermediate, but also two other intermediates. All three of the intermediates resulting from the present process with 25–45 molar excess of acrylic acid have been found to be hydrolyzable to 2-carboxyethyl(phenyl)phosphinic acid.

In contrast to the present process, if only a molar equivalent of acrylic acid is used according to the prior art reference, the yield of desired acid is unsatisfactory and the product of hydrolysis is a mixture of difficult to separate phosphorus-containing acids.

It has been found that a markedly increased yield of pure 2-carboxyethyl(phenyl)phosphinic acid can be obtained by using a specific proportion of acrylic acid, 25–45% molar excess (preferably 30–40% excess), to consume all of the dichloro(phenyl)phosphine reactant. In this way one obtains a mixture of three intermediates, III-V, below, each of which can be readily hydrolyzed to the desired product. In this way essentially all of the dichloro(phenyl)phosphine is converted to 2-carboxyethyl(phenyl)phosphinic acid (I), as illustrated in the following equation using 35% molar excess of acrylic acid.

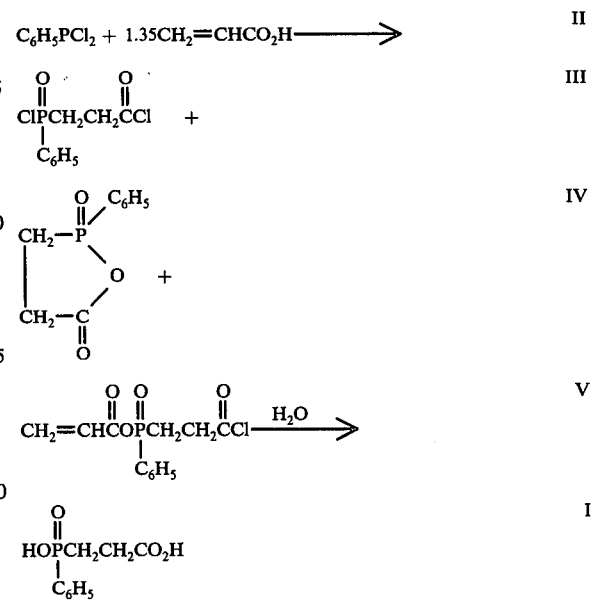

No solvent is required in the first step. However, inert solvents, for example, toluene or chlorobenzene, can be used. The acrylic acid is normally added to stirred dichloro(phenyl)phosphine at 80° to 150° C, preferably at 90°–120° C. The conversion of the reactants to intermediates III-V is nearly complete at the end of the acrylic acid addition, but the mixture may be stirred and warmed for an additional period, say one-half to five hours.

For the hydrolysis step, water can be added to the mixture of intermediates III-V, possibly in a solvent to aid mixing, but it is preferred to add the undiluted mixture of III-V to at least enough water to complete hydrolysis to I. It is advantageous to use excess water to aid stirring and temperature control. About 5 to 15 molar excess of water has been found convenient. The hydrolysis can be carried out from 0° to about 100° C. It has been found useful to regulate the amount of water used and the reaction temperature so that product I dissolves in the water as it is formed. Cooling of the reaction mixture while being stirred then causes most of I to separate in good quality crystalline form. The 5–15% of I that is dissolved in the filtrate can be recovered by standard procedures. In this way a substantially quantitative yield of I is obtained, based on the dichloro(phenyl)phosphine that is used.

The following example illustrates specific embodiments of the invention but are not limitative of the scope of the invention.

EXAMPLE 1

2-Carboxyethyl(phenyl)phosphinic Acid(I).

Dichloro(phenyl)phosphine, 716g (4.0 moles), is stirred and warmed to 90° C. The dropwise addition of acrylic acid is started, and warming is continued to 105° C, after which the heat of reaction is sufficient to employ moderate cooling of the reaction vessel. The addition of acrylic acid is then carried out at 105°–110° C until 288g (4.0 moles) is added. Warming at 105° is continued for 0.5 hr. An analytical sample shows a $^{31}$P nmr signal for about 25% of the total phosphorus at −161.6 ppm for unreacted dichloro(phenyl)phosphine. Continued addition of acrylic acid to a 35% molar excess, corresponding to 389g (5.4 moles) is conducted at 105°–110° C. The $^{31}$P nmr measurement now shows that all of the dichloro(phenyl)phosphine has been consumed. Further, $^{31}$P nmr measurement of the reaction mixture shows three signals: −52.2 ppm for 3-(chlorophenylphosphinyl)propionyl chloride (III) (70%); −50.5 ppm for the cyclic anhydride of 2-carboxyethyl(phenyl)phosphinic acid(IV) (15%); and −39.6 ppm for the anhydride of acrylic acid and 3-chlorocarbonylethyl(phenyl)phosphinic acid(V)(15%). This mixture of III, IV, and V is then added to two liters of water with stirring and cooling below 55° C during 2.5 hrs. The white slurry is cooled to 10° C, filtered, and the solid is washed with water and dried, giving 767.5g (89.6% yield) of 2-carboxyethyl(phenyl)phosphinic acid (I), a white solid; m.p. 158°–161° C. (from H$_2$O); $^{31}$P nmr(DMSO-d$_6$) −37.2 ppm.

Anal. Calcd. for C$_9$H$_{11}$O$_4$P: C, 50.48; H, 5.18; P, 14.46. Found: C, 50.30; H, 5.02; P, 14.53.

Most of the excess water is stripped from the filtrate at reduced pressure, and the residue is filtered, giving additional white solid, I.

What is claimed is:

1. Process for the production of 2-carboxyethyl(phenyl)phosphinic acid which comprises admixing at a temperature of 80° to 150° C dichloro(phenyl)phosphine with acrylic acid in the proportion of from 25 to 45% molar excess of the acrylic acid to obtain a mixture of 3-(chlorophenylphosphinyl)propionyl chloride, and the cyclic anhydride of 2-carboxyethyl(phenyl)phosphinic acid, and the mixed anhydride of acrylic acid with 3-chlorocarbonylethyl(phenyl)phosphinic acid, and thereafter hydrolyzing the said mixture with water.

2. Process for the production of 2-carboxyethyl(phenyl)phosphinic acid which comprises admixing at a temperature of 80° to 150° C dichloro(phenyl)phosphine with acrylic acid in the proportion of from 25 to 45% molar excess of the acrylic acid to obtain a mixture of 3-(chlorophenylphosphinyl)propionyl chloride, and the cyclic anhydride of 2-carboxyethyl(phenyl)phosphinic acid, and the mixed anhydride of acrylic acid with 3-chlorocarbonylethyl(phenyl)phosphinic acid, and thereafter hydrolyzing the said mixture with water in the proportion of 5 to 15 molar excess at a temperature of 0° to 100° C.

3. Process for the production of 2-carboxyethyl(phenyl)phosphinic acid which comprises admixing at a temperature of 80° to 150° C dichloro(phenyl)phosphine with acrylic acid in the proportion of from 25 to 45% molar excess of acrylic acid and then hydrolyzing the resulting mixture with water at 0° to 100° C.

4. Process as in claim 3 in which the water is present as a 5 to 15 molar excess of water.

* * * * *